US006463315B1

(12) United States Patent
Klingberg et al.

(10) Patent No.: US 6,463,315 B1
(45) Date of Patent: Oct. 8, 2002

(54) ANALYSIS OF CEREBRAL WHITE MATTER FOR PROGNOSIS AND DIAGNOSIS OF NEUROLOGICAL DISORDERS

(75) Inventors: Torkel Klingberg, Palo Alto; Maj Hedehus, Mountain View; John D. E. Gabrieli, Stanford; Michael E. Moseley, Redwood City, all of CA (US); Russell A. Poldrack, Cambridge, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/491,986

(22) Filed: Jan. 26, 2000

(51) Int. Cl.[7] .............................................. A61B 5/055
(52) U.S. Cl. ........................ 600/410; 600/419; 324/309
(58) Field of Search ................................. 600/410, 419, 600/544, 545; 324/307, 309, 306

(56) References Cited

U.S. PATENT DOCUMENTS

| | | | |
|---|---|---|---|
| 4,442,404 A | 4/1984 | Bergmann | 324/309 |
| 5,539,310 A | 7/1996 | Basser et al. | 324/307 |
| 5,560,360 A * | 10/1996 | Filler et al. | 600/408 |
| 5,969,524 A * | 10/1999 | Pierpaoli et al. | 324/307 |
| 6,061,587 A * | 5/2000 | Kucharczyk et al. | 600/411 |
| 6,288,540 B1 * | 9/2001 | Chen et al. | 324/300 |

OTHER PUBLICATIONS

"Diffusion Tensor Microimaging", downloaded Sep. 23, 1999 from http://csbnmr.health.ufl.edu/~binglis/dtensor.html.

"$1.1 Million Grant to Study Brain Injury in Newborns", Feb. 26, 1999 press release, downloaded Sep. 23, 1999 from http://medicine.wustl.edu/~wumpa/news/newborn-brain.html.

"Brain Signature for Dyslexia Found", Mar. 3, 1998 The Living Channel, downloaded Sep. 22, 1999 from http://www.desertmail.com/content/living/3_98/brain_3.3.98.shtml.

"Magnetic Resonance Imaging (MRI)", from National Institute of Mental Health, downloaded Sep. 22, 1999 from http:/www.nimh.nih.gov/hotsci/mri.htm.

"Atypical Brain Activity Detected In People With Dyslexia", Bethesda, MD, Jul. 3, 1996; downloaded Sep. 22, 1999 from http:/www.kidsource.com/kidsource/content/news/brain7_9_96.html.

Baratti et al., "Comparative MR imaging study of brain maturation in kittens with T1, T2, and the trace of the diffusion tensor," *Radiology,* 210(1):133–142 (1999) Abstract.

Basser et al., "MR Diffusion tensor spectroscopy and imaging," *Biophys J.,* 66(1):259–267 (1994) Abstract.

Basser, P.J., "Inferring microstructural features and the physiological state of tissues from diffusion–weighted images," *NMR Biomed.,* 8(7–8):333–344 (1995) Abstract.

(List continued on next page.)

*Primary Examiner*—Shawna J Shaw
(74) *Attorney, Agent, or Firm*—Townsend and Townsend and Crew LLP; Henry K. Woodward

(57) ABSTRACT

A method of detecting a neurological disorder such as dyslexia includes the steps of measuring microstructure of cerebral white matter, and correlating the microstructure to the presence of the neurological disorder. For dyslexia, the white matter is confined to temporo-parietal white matter. The microstructure is measured by determining cerebral white matter anisotropy using diffusion tensor magnetic resonance imaging (DTI).

6 Claims, 3 Drawing Sheets

OTHER PUBLICATIONS

Basser et al., "Microstructural and physiological features of tissues elucidated by quantitative–diffusion–tensor MRI," *J. Magn. Reson. B,* 111(3):209–219 (1996) Abstract.

Basser et al., "A simplified method to measure the diffusion tensor from seven MR images," *Magn. Reson. Med.,* 39(6):928–934 (1998) Abstract.

Bastin et al., "The use of diffusion tensor imaging in quantifying the effect of dexamethasone on brain tumours," *Neuroreport,* 10(7):1385–1391 (1999) Abstract.

Buchsbaum et al., "MRI white matter diffusion anisotropy and PET metabolic rate in schizophrenia," *Neuroreport,* 9(3):425–430 (1998) Abstract.

Chien et al., "MR diffusion imaging of the human brain," *J. Comput. Assist Tomogr.,* 14(4):514–520 (1990) Abstract.

Dalby et al., "Temporal lobe asymmetry and dyslexia: an in vivo study using MRI," *Brain Lang.,* 62(1):51–69 1998 Abstract.

Demb et al., "Functional Magnetic Resonance Imaging of Early Visual pathways in Dyslexia," *J. Neuroscience,* 18:6939–6951 (1998) Abstract downloaded Sep. 22, 1999 from http:/white.stanfor.edu/~heeger/publications.html.

Duara et al., "Neuroanatomic differences between dyslexic and normal readers on magnetic resonance imaging scans," *Arch. Neurol.,* 48(4):410–416 (1991) Abstract.

Harada et al., "Diffusion imaging of the human brain: a new pulse sequence application for a 1.5–T standard MR system," *AJNR Am. J. Neuroradiol.* 12(6):1143–1148 (1991) Abstract.

Horsfield et al., "Diffusion magnetic resonance imaging in multiple sclerosis," *J. Neurol. Neurosurg. Psychiatry,* 64 (suppl 1):S80–S84 (1998) Abstract.

Hugdahl et al., "Central auditory processing, MRI morphometry and brain laterality: applications to dyslexia," *Scand. Audiol. Suppl.,* 49:26–34 (1998) Abstract.

Huppi et al., "Microstructural development of human newborn cerebral white matter assessed in vivo by diffusion tensor magnetic resonance imaging," *Pediatr. Res.,* 44(4):584–590 (1998) Abstract.

Hynd et al., "Brain morphology in development dyslexia and attention deficit disorder/hyperactivity," *Arch. Neurol.,* 47(8):919–926 (1990) Abstract.

Jones et al., "Characterization of white matter damage in ischemic leukoaraiosis with diffusion tensor MRI," *Stroke,* 30(2):393–397 (1999) Abstract.

Jones et al., "Optimal strategies for measuring diffusion in anisotropic systems by magnetic resonance imaging," *Magn. Reson. Med.,* 42(3):515–525 (1999) Abstract.

Jones et al., "Non–invasive assessment of axonal fiber connectivity in the human brain via diffusion tensor MRI," *Magn. Reson. Med.,* 42(1):37–41 (1999) Abstract.

Kushch et al., "Temporal lobe surface area measurements on MRI in normal and dyslexic readers," *Neuropsychologia,* 31(8):811–821 (1993) Abstract.

Larsen et al., "MRI evaluation of the size and symmetry of the planum temporale in adolescents with developmental dyslexia," *Brain Lang.,* 39(2):289–310 (1990) Abstract.

Le Bihan et al., "Diffusion MR imaging: clinical applications," *AJR Am. J. Roentgenol.,* 159(3):591–599 (1992) Abstract.

Lim et al., "Compromised White Matter Tract Integrity in Schizophrenia Inferred From Diffusion Tensor Imaging," *Arch. Gen. Psychiatry,* 56:367–374 (1999).

Matthews et al., "Functional magnetic resonance imaging: clinical applications and potential," *J. Inherit Metab. Dis.,* 22(4):337–352 (1999) Abstract.

Moseley et al., "Diffusion–weighted MR Imaging of Anisotropic Water Diffusion in Cat Central Nervous System," *Radiology,* 176:439–445 (1990).

Nidecker, A., "Imaging details the Neural Disruption Linked to Dyslexia," *Clin. Psychiatry News,* 26(4):1 (1998), downloaded Sep. 22, 1999 from http://patient.medscape.com/IMNG/ClinPsychNews/1998/v26.n04/cpn2604.01.01.html.

Pierpaoli et al., "Diffusion tensor MR imaging of the human brain," *Radiology,* 201(3):637–648 (1996) Abstract.

Pierpaoli et al., "Toward a quantitative assessment of diffusion anisotrophy," *Magn. Reson. Med.,* 36(6):893–906 (1997) Abstract.

Rowley et al., "Diffusion MR imaging. Theory and applications," *Neuroimaging Clin. N. Am.,* 9(2):343–361 (1999) Abstract.

Rumsey et al., "Corpus callosum morphology, as measured with MRI, in dyslexic men," *Biol. Psychiatry,* 39(9):769–775 (1996) Abstract.

Rumsey et al., "A magnetic resonance imaging study of planum temporale asymmetry in men with developmental dyslexia," *Arch. Neurol.,* 54(12):1481–1489 (1997) Abstract.

Schultz et al., "Brain morphology in normal and dyslexic children: the influence of sex and age," *Ann. Neurol.,* 35(6):732–742 (1994) Abstract.

Shimony et al., "Quantitative diffusion–tensor anisotrophy brain MR imaging: normative human data and anatomic analysis," *Radiology,* 212(3):770–784 (1999) Abstract.

Sorensen et al., "Human acute cerebral ischemia: detection of changes in water diffusion anisotrophy by using MR imaging," *Radiology,* 212(3):785–792 (1999) Abstract.

Tofts, P.S., "Novel MR image contrast mechanisms in epilepsy," *Magn. Reson. Imaging,* 13(8):1099–1106 (1995) Abstract.

Ulug et al., "Clinical use of diffusion–tensor imaging for diseases causing neuronal and axonal damage," *AJNR Am. J. Neuroradiol.,* 20(6):1044–1048 (1999) Abstract.

* cited by examiner

ANALYSIS OF CEREBRAL WHITE MATTER FOR PROGNOSIS AND DIAGNOSIS OF NEUROLOGICAL DISORDERS

STATEMENT AS TO RIGHTS TO INVENTIONS MADE UNDER FEDERALLY SPONSORED RESEARCH AND DEVELOPMENT

The U.S. Government has rights in the invention pursuant to NIH Grant No. P41-RR09784 to Stanford University.

BACKGROUND OF THE INVENTION

This invention relates generally to the study of neurological disorders, and more particularly the invention relates to the use of magnetic resonance imaging techniques to study the microstructural integrity of cerebral white matter to ascertain the presence of a neurological disorder such as dyslexia or the likelihood of developing such a neurological disorder.

The use of diffusion tensor magnetic resonance imaging (DTI) for imaging anisotropic tissue such as brain white matter is known. See M. E. Moseley et al., "Diffusion-weighted MR Imaging of Anisotropic Water Diffusion in Cat Central Nervous System," Radiology, 176, 439 (1990); P. J. Basser, J. Mattiello, and D. Le Bihan, "Estimation of the Effective Self-Diffusion Tensor from the NMR Spin Echo," JMR B 103, 247–254 (1994); P. J. Basser, "Inferring Microstructural Features and the Physiological State of Tissues from Diffusion-Weighted Images," NMR in Biomed 8, 333–344 (1995); P. J. Basser and C. Pierpaoli, "Microstructural and physiological features of tissues elucidated by quantitative-diffusion-tensor MRI," J. Magn Reson B 111, 209–219 (1996); C. Pierpaoli, P. Jezzard, P. J. Basser, A. Barnett, and G. Di Chiro, "Diffusion Tensor MR Imaging of the Human Brain," Radiology 201, 637–648 (1996); C. Pierpaoli and P. J. Basser, "Toward a Quantitative Assessment of Diffusion Anisotropy," MRM 36, 893–906 (1996); C. Pierpaoli, A. Barnett, A. Virta, L. Penix, and R. Chen, "Diffusion MRI of Wallerian Degeneration. A New Tool to Investigate Neural Connectivity in vivo?" Proc. ISMRM 6th Meeting, Sydney (1998) 1247; and Lim et al., "Compromised White Matter Track Integrity in Schizophrenia Inferred From Diffusion Tensor Imaging," Arch Gen Psychology/Vol. 56, April 1999. DTI provides a novel way to characterize tissues based on sensitivity to microscopic molecular motion of water. Clinical implementation requires strong, fast hardware and careful post processing of diffusion parameters. Diffusion weighted images and derivatives such as the three principal diffusivities of the diffusion tensor are quite specific in reflecting the physical properties of diffusion.

Diffusion weighted imaging (DI) consists of estimating the effective scalar diffusivity of water, D, in each voxel from a set of diffusion weighted images. During the time of a typical magnetic resonance data acquisition, water molecules diffuse on the order of a few microns, which is comparable to the dimensions of cellular structures, but significantly less than the dimensions of a voxel. Since D is sensitive to the physical properties, composition and spatial distribution of the tissue constituents, the measurement is sensitive to the tissue microstructure and physiological state.

Diffusion along a given axis is typically measured by placing a pair of diffusion sensitizing gradient pulses in the same axis in the magnetic resonance (MR) pulse sequence. The gradient pulses impose position-dependent phases on water protons that are equal in magnitude but opposite in sign and therefore cancel for stationary spins. However, for protons that move between the two gradient pulses, a finite net phase is accumulated. The sum of all phases from all protons results in attenuation of the MR signal due to interference effects. The magnitude of signal attenuation is dependent on the diffusivity of water, and the width, separation and amplitude of the gradient pulses. In a generalized case where the diffusivity may differ in different directions, a diffusion tensor matrix notation is used.

The present invention is directed to the use of DTI for the prognosis and diagnosis of a dyslexic neurologic disorder. Reading is a complex cognitive skill that requires multimodal processing of visual symbols, speech sounds (known as phonology), and linguistic entities such as words and sentences. Studies using neuroimaging have demonstrated that a widespread set of brain regions are engaged during reading tasks, highlighting the need for communication between these regions in skilled readers. About 5–10% of children, however, exhibit developmental dyslexia, an impairment in learning to read despite adequate instruction and normal intelligence. Dyslexia is associated with deficits in language processing beyond reading, particularly in the processing of phonology. In addition, dyslexic individuals exhibit deficits in nonlinguistic perceptual processing, particularly on tasks requiring the processing of rapidly transient auditory and visual signals.

A growing body of evidence suggests that dyslexia is a neurologically-based disorder perhaps with a genetic basis. Postmortem studies of dyslexic brains have discovered a consistent pattern of neuropathological changes (cortical Microlesions and glial scars) throughout the left perisylvian cortices, along with reduced left-right asymmetry of the planum temporale. Functional magnetic resonance imaging (fMRI) studies of dyslexia have found atypical activation patterns in temporo-parietal cortex during reading tasks, particularly those involving the recoding of written symbols in their phonological counterparts. Studies using neuromagnetic imaging have also found differences in the time course of cortical processing in dyslexic individuals compared to normal readers. Each of these findings is consistent with a neural basis for dyslexia, but the underlying cause of these differences in neural processing is not currently known.

Two studies have suggested that developmental dyslexia may represent a disconnection syndrome in which communication is impaired between temporo-parietal cortices and other brain regions such as frontal cortex. In particular, dyslexic individuals have exhibited decreased correlations of cortical activity between areas involved in reading, which may indicate that a communication between these areas is impaired. Another study has proposed such a disconnection on the basis of abnormal patterns of activation in the temporo-parietal, frontal, and insular cortices in dyslexic adults. This proposal is consistent with behavioral evidence that dyslexic individuals are impaired at the cross-modal mapping of visual and auditory information. The impaired communication could be the results of a structural disturbance or disruption. However, the nature and cause of a putative structure disruption is currently unknown.

A plausible locus for such a disruption in communication is the white matter tracts connecting tempora-parietal and frontal cortices, but to date there is no consistent evidence of white matter disturbance in dyslexia. Although a number of previous studies have examined the differences in neuroanatomical structure between dyslexic individuals and normal readers, these studies have focused primarily of hemispheric asymmetry of the planum temporale and differences in corpus callosum size, with mixed results in each of those areas. None of these studies has demonstrated specific differences in white matter morphology, but the imaging techniques used in these studies (such as T1-weighted structural MR imaging) can only image macrostructural features of white matter. A postmortem study of a single dyslexic individual revealed increased white matter volume in the left hemisphere and enlarged neurons in the cortex extending into the subcortical white matter. Subsequent postmortem studies, however, were focused on gray matter, and did not report white matter abnormalities in dyslexia.

SUMMARY OF THE INVENTION

In accordance with the invention, an objective and non-invasive measure of neural density and integrity in cerebral white matter is used to assess verbal and non-verbal mental skills and abilities. These measures, which reflect the organization of white matter structures in the central nervous system, can be used to predict verbal and non-verbal cognitive processing or capacity (such as word skill scores) in children as well as adults. This provides a quantitative indication of neuronal fiber density, integrity, myelination, and coherence. These measures, which reflect the organization of white matter structures in the CNS, can be used to predict verbal and non-verbal cognitive processing or capacity (such as word skill scores) in children as well as adults.

In accordance with a specific application of the invention a method of analyzing cerebral white matter for use in the prognosis and diagnosis of a dyslexic neurological disorder includes the steps of a) measuring the microstructure of cerebral white matter, b) determining communication tracts in the cerebral white matter for the measured microstructure, and c) correlating communication tracks to the presence of a dyslexic disorder. More particularly, the microstructure is determined by diffusion anisotropy in the cerebral white matter. Anisotropy is a measure that quantifies the degree to which water diffusion differs in three dimensions. The DTI technique is based on sensitizing the magnetic resonance (MR) signal to movement of water on the order of microns and determining the magnitude and direction of the water diffusion in three dimensions. In white matter of the brain, diffusion of water perpendicular to the direction of the axons for communication tracks is restricted by the myelin sheath and cell membrane such that diffusion will be greater along the length of the axon than perpendicular to the axon.

The invention and objects and features thereof will be more readily apparent from the following detailed description and dependent claims when taken with the drawing.

DETAILED DESCRIPTION OF ILLUSTRATIVE EMBODIMENTS

Figure 1A:
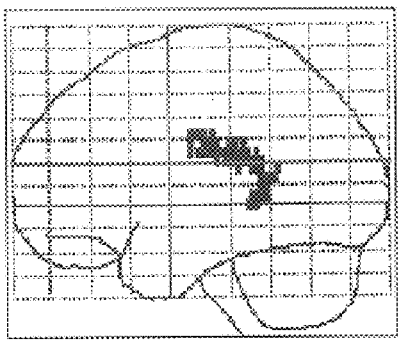
FIGS. 1A, 1B, 1C are respectively a sagittal projection of a left hemisphere cluster where there is a significant difference in anisotropy, an axial slice from an anisotropy image of a control subject, and a part of the image of FIG. 1B shown in higher magnification.

The invention will be described with reference to the use of diffusion tensor imaging (DTI) in measuring anisotropy in cerebral white matter for diagnosing a neurological disorder and in the prognosis of a developing neurological disorder. However, the invention can be applied to other disease states and disabilities and deficit disorders.

Anisotropy in myelinated white matter is likely to be determined by a number of microstructure features: the integrity of axonal cell membranes, the amount and integrity of myelin around the axons, the coherence of axonal orientation, and the number and size of axons. In particular, anisotropy has been noted to vary directly with myelination. Increased myelination is associated with greater anisotropy. Diffusion anisotropy in white matter correlates with histological markers of myelination, with the development course of myelination in newborns and young children, and with demyelination in multiple sclerosis.

If the reading deficit in dyslexia is due to a structural disturbance of the white matter tracts connecting anterior and posterior cortical regions, this disturbance may be reflected in lower anisotropy values. To test this hypothesis, six adults who had been previously diagnosed with development dyslexia and eleven control adults were studied with DTI. Anisotropy of diffusion was measured in the entire brain of each individual, the images were normalized to a standard anatomical space, and the anisotropy of the dyslexic group was compared to that of the control group. High-resolution T1-weighted anatomical images were also collected, which reveal anatomical structure but are not sensitive to diffusion anisotropy. With these measures, both the location and the nature of any white matter disturbance in dyslexia could be evaluated for the first time.

DTI can also provide insights into a fundamental question about developmental dyslexia: Should dyslexia be considered as a discrete neurological syndrome or as the tail end of a normal distribution of neural function? A number of previous studies have identified differences between dyslexic and normal readers using structural neuroimaging, functional neuroimaging, and postmortem neuropathology, and such findings are consistent with the conceptualization of dyslexia as a discrete pathological syndrome. Most of these studies, however, have focussed on group differences and have not analyzed variation within the two groups. Behavioral evidence from a sample of 414 readers, however, indicates that dyslexia may be more appropriately described as the tail end of a normal distribution of reading ability. This view of dyslexia suggests that neural factors underlying differences in reading ability between normal and dyslexic groups may differ across the range of normal reading ability as well. However, no previous studies have reported a quantitative relation between neural structure or function and reading ability in normal readers.

In order to examine this question, we administered reading tests to each of the dyslexic and control subjects in our study, and examined the correlation of white matter anisotropy with reading scores both overall and within each group separately. If dyslexia represents one end of a continuous distribution in underlying white matter structure, then any correlations between white matter structure and reading behavior should extend across the control group as well as the dyslexic group.

Group Comparison

Figure 1B:
Figure 1C:
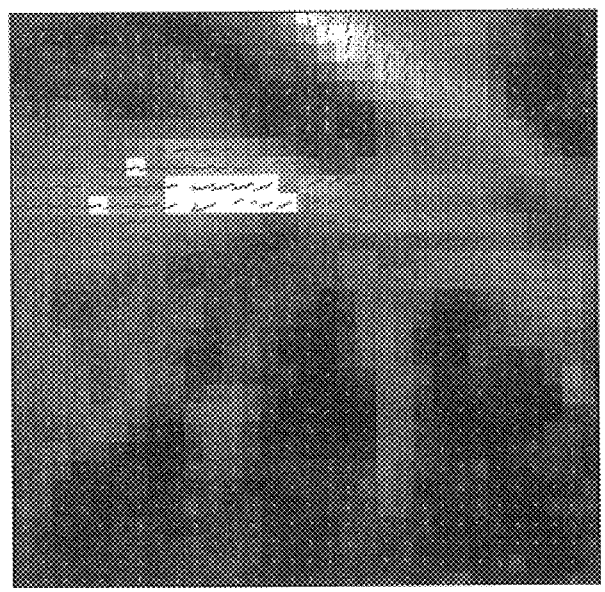

The dyslexic group showed significantly lower anisotropy only in two regions, located bilaterally in the white matter in the temporo-parietal region of the brain ($P<0.05$, one-tailed, corrected for multiple comparisons) (FIGS. 1A–1C). An identical statistical comparison of the high resolution T1-weighted anatomical images failed to show any differences between the groups ($P>0.98$, one-tailed, corrected). Autocorrelation (smoothness) between voxels within images was slightly lower in the T1-weighted images than in the anisotropy images, which could possible have affected the outcome of the statistical analysis. A second analysis was therefore performed after filtering T1-weighted images with a Gaussian kernel in three dimensions to an autocorrelation that matched the anisotropy images. This reanalysis also failed to show any significant differences in T1 images between the groups (P>0.56, corrected). In addition, T1 signal differences specifically in the two VOIs was measured, but no group differences were found (t-tests, P>0.74 for both VOIs). Thus, the observed group difference was specific to the tissue properties measured by diffusion rather than to any gross anatomical differences, such as gyral pattern or white matter volume.

Correlations with Reading Ability

Figure 2:
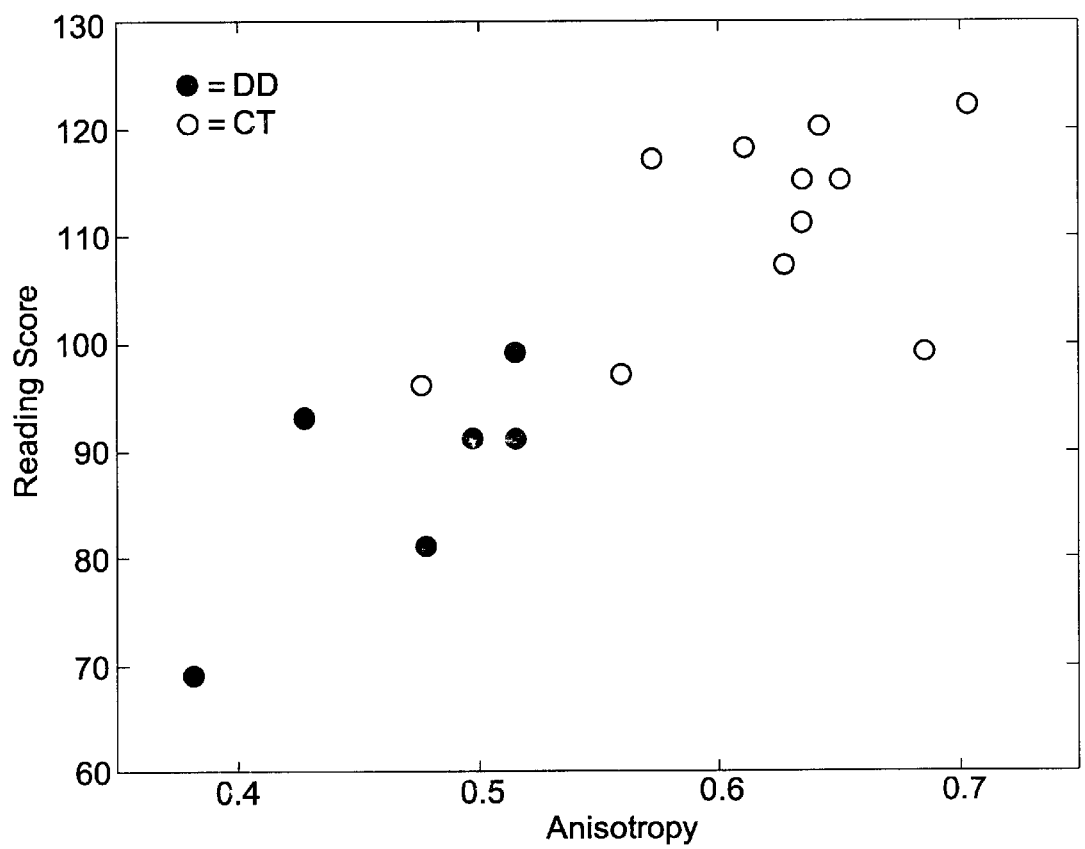
FIG. 2 is a plot of anisotropy versus reading score for dyslexic group (DD) and control group (CT).

To test the behavioral relevance of the group difference in anisotropy, each subject performed a standardized measure of reading ability: the Word Identification Subtest (Word ID) from the Woodcock Reading Mastery Tests—Revised (Woodcock, 1987). In the Word ID task, single words of increasing complexity are visually presented and subjects are asked to pronounce them. A correlation analysis was performed to find voxels anywhere in the brain with a positive correlation between anisotropy scores and the Word ID score (correcting for the large number of comparisons), the correlation analysis revealed one cluster of significantly correlated voxels in the left hemisphere which overlapped (52% of voxels) with the left temporo-parietal region found in the between-group anisotropy comparison (P<0.001 for the entire region, one-tailed, corrected). No overlap was found with the right temporo-parietal region, and the rest of the analysis was therefore restricted to the left VOI. The maximum correlation in the left temporo-parietal region was r=0.84, for the entire group (FIG. 2).

In order to determine whether the correlation between reading ability and anisotropy reflected a group difference or a continuous relation, we examined the correlation between reading ability and anisotropy scores separately in each group. A significant correlation was observed in both the dyslexic (r=0.74, P<0.05, one-tailed) and the control (r=0.53, P<0.05, one-tailed) groups taken alone in the location exhibiting maximal correlation in the group analysis. Thus, the relationship between white matter microstructure and reading ability does not simply reflect a difference between dyslexic and control groups, but rather reflects a continuous structure-function relationship encompassing both normal and impaired readers.

A second reading test was also administered: the Word Attack Subtest of the Woodcock Reading Mastery Test, in which subjects are asked to pronounce pseudowords. The anisotropy values in the region that correlated maximally with the Word ID score also correlated with this second reading task for the entire group (r=0.65, P<0.01, one-tailed), demonstrating the generality of the relation between reading function and white matter microstructure.

The foregoing analysis was performed on anisotropy values that were normalized by scaling to the global image mean. In order to determine whether this scaling affected the pattern of results, data were also analyzed using unscaled anisotropy values. A significant correlation between Word ID score and mean anisotropy within the left temporo-parietal VOI from the correlation analysis was found using these unscaled values (r=0.72, P<0.001).

An additional analysis was performed in which effects of age and gender were removed as confounds prior to correlation between anisotropy and the Word ID score. This analysis gave similar results to the first SPM analysis, with maximum correlation in the same voxel (x=−28, y=−20, z=28; P<0.05, corrected).

The mean unscaled anisotropy values in the VOI was 0.59±0.02 for the control and 0.46±0.03 for the dyslexic group (t=4.88, P<0.0002). The corresponding numbers for the right VOI were 0.56±0.01 and 0.38±0.04, for the control and dyslexic group respectively. The values obtained from the group comparison analysis showed a significant correlation with reading scores (r=0.77, P<0.0003), and the values obtained from the correlation analysis showed a significant group difference (P<0.0001).

Directional Analyses

Figure 3:
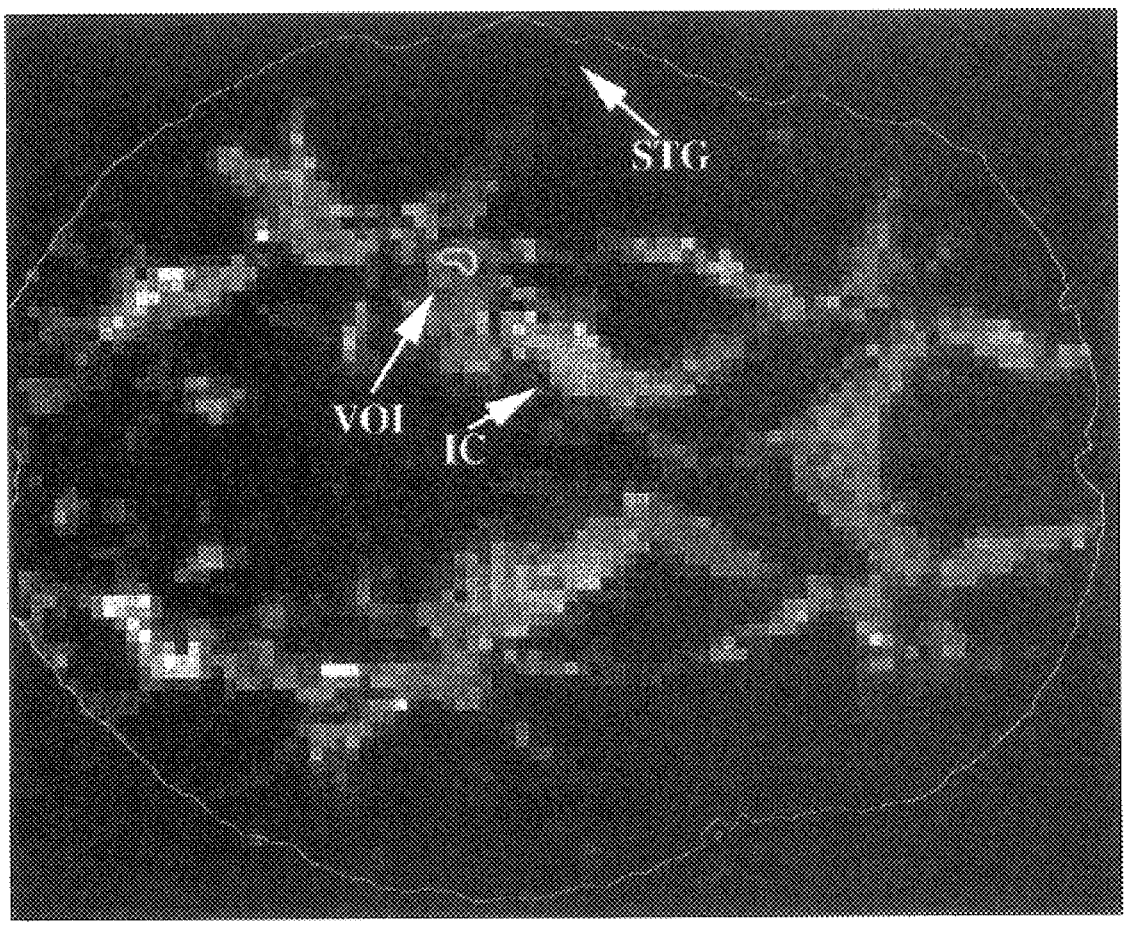
FIG. 3 is a DTI image illustrating orientation of axons in imaged voxels.

In addition to providing information about anisotropy, DTI also provides information about the orientation of the axons in each voxel (see FIG. 3). The regularity, or coherence, of this direction between voxels can therefore be measured and quantified as a coherence index. There is currently no technique for estimating specifically the coherence within voxels. No significant group difference in coherence was observed within the VOI (P>0.97). This result suggests that differences in anisotropy between dyslexic and control groups likely reflect differences in axonal structure (e.g., myelination) rather than differences in the coherence of axonal orientation.

In order to determine the orientation of white matter tracts in the group-difference VOI, the orientation of diffusion in each voxel was classified as either anterior-posterior, left-right, or inferior-superior. Fifty-six percent (±4%) of the voxels in the VOI exhibited anterior-posterior orientation, consistent with the involvement of these white-matter tracts in cortico-cortical communication both within the temporo-parietal region and between temporo-parietal and frontal regions. The proportion of anterior-posterior voxels was less than 100% indicating that the VOI was not confined to anterior posterior axons, but was significantly more than the 33% that would be expected if orientation was random (P<0.001).

DISCUSSION

Using diffusion tensor MR imaging, differences in white matter microstructure between normal readers and individuals with a history of developmental dyslexia were found bilaterally in the temporo-parietal white matter underlying perisylvian cortical areas. No differences in T1-weighted MR signal were found in these regions, demonstrating that the differences were specific to the microstructural features measured by diffusion anisotropy. Measurement of intervoxel coherence demonstrated no differences between groups, suggesting that the group difference in anisotropy primarily reflects differences in axonal structure such as myelination. An overlapping region in the left temporo-parietal white matter exhibited significant correlation between white matter microstructure and reading ability in all 17 subjects. This correlation was also apparent within the control group taken alone, demonstrating for the first time a structural neural correlate of reading ability in normal readers.

These results point to a critical role in reading of white matter underlying temporo-parietal cortex in the left hemisphere. Left temporo-parietal cortex has long been associated with reading; lesions in this region resulting in acquired dyslexias such as including alexia with agraphia and deep dyslexia. Previous neuroinaging studies of adults with developmental dyslexia have found abnormally reduced activation in temporo-parietal cortex during reading tasks requiring phonological processing and abnormally low correlation of metabolic activity between temporo-parietal cortex and other cortical areas during these same tasks. The location of the white matter disturbance identified by DTI is thus convergent with other forms of evidence that indicate the essential role of this brain region for reading.

The white matter disturbance in dyslexia discovered using DTI likely affects white matter tracts connecting these temporo-parietal areas with each other and with other brain regions. Case studies of white matter anatomy using postmortem dissection and DTI show that this left temporo-parietal region contains sagittally oriented axons in the external capsule and the arcuate fasciculus that project from occipital, inferior parietal, and temporal cortex to the frontal cortex. These findings are consistent with our DTI analysis showing that axons in the region of interest were predominantly oriented in the anterior-posterior direction. The present finding thus demonstrates a plausible structural basis for the functional disconnection of temporo-parietal and frontal cortices that has been previously suggested to occur in developmental dyslexia. Weak myelination or structural disruption of the white matter tracts connecting temporoparietal cortex and other cortices would impair communication between these areas and could thereby impair the combination of visual and phonological codes that is necessary for skilled reading.

White Matter and Rapid Perceptual Processing

Although developmental dyslexia is defined as a deficit in reading, there is strong evidence demonstrating impairments of perceptual processing of both verbal and nonverbal stimuli in dyslexia, particularly for rapidly transient auditory stimuli and moving visual stimuli. The processing of transient auditory information is particularly important for the perception of phonology, in which essential contrasts are defined by acoustic information changing rapidly over tens of milliseconds. Deficits in visual motion processing may interfere with other aspects of reading, such as the accurate visual perception of letter position.

A disturbance of white matter microstructure provides a plausible explanation for multimodal deficits in the processing of rapidly transient signals. In particular, intact myelination is important for rapid conduction of neural impulses, and a disturbance of myelination would be particularly detrimental for accurate coding and transmission of rapidly transient signals. In vision, rapid transient signals are especially associated with the perception of movement, and two fMRI studies have reported diminished activations in area MT, an area specialized for visual motion perception, in dyslexic individuals. The reduction in MT activation correlated with reading impairment. The importance of myelination for area MT processing is evident from the exceptional degree of myelination in that area relative to adjacent cortices. Furthermore, the particular location of the white matter difference in anisotropy found in the present study, which could contain fibers form both auditory and visual cortices, provides a possible explanation for the correlation that has been observed between deficits in rapid auditory and visual processing. Thus, the present findings are consistent with findings that myelination is especially important for processing rapidly transient signals, and that dyslexia may often be characterized by disproportionate deficits in processing such signals.

Structure-Function Relations In Dyslexic And Normal Readers

The data presented here provide evidence that the microstructure of white matter is related to reading ability, such that greater anisotropy is correlated with superior reading performance. Furthermore, this relationship extended across both dyslexic and normal reading groups, and the correlation between reading ability and white matter structure was evident within each group. One interpretation of these data is that the microstructure associated with developmental dyslexia represented one end of a continuous distribution. By this view, reading difficulty becomes apparent when white matter integrity falls below some threshold. This would also be consistent with the behavioral studies showing that dyslexia may be more appropriately described as the tail end of a normal distribution of reading ability.

However, the finding of a correlation of white matter microstructure and reading in both dyslexic and non-dyslexic subjects does not exclude that there also could be a neurological insult affecting white and gray matter in dyslexic subjects, but the present findings show that it is not necessary to presuppose an insult in order to explain the deficits in reading. Discrete pathology in dyslexic subjects has been reported in the perisylvian cortices. The finding of quantitative differences in thalamic structure between dyslexic and normal readers is more easily reconciled with a continuous nature of structure and function.

Because of the correlational nature of the present study, it is not possible to directly determine whether the differences in reading ability are caused by differences in white matter structure or follow from the acquisition of reading skill. Comparisons of literate and illiterate adults have demonstrated that literacy changes the functional anatomy of speaking, and it is plausible that learning to read exerts other powerful changes on brain organization as well. These questions can be most directly addressed by longitudinal studies examining whether white matter structure in preliterate children predicts reading performance and whether white matter exhibits specific changes related to reading acquisition.

We have recognized that diffusion tensor imaging offers considerable promise for extending the range of neuroimaging in cognitive neuroscience. Functional neuroimaging techniques, including positron emission tomography and functional magnetic resonance imaging have become important for identifying gray matter contributions to cognition. The present invention of a correlation between reading skill and white matter structure reveals that DTI may provide a complimentary method for imaging white matter contributions to cognition. DTI has been used, for example, to demonstrate separable contribution of axonal structure and directional coherence to brain development and to hemispheric asymmetry. DTI is safe and noninvasive, which makes it suitable for a wide range of subjects, including young children and patients.

DTI is particularly useful because it does not require any active participation on the part of the subject during scanning, unlike functional imaging techniques such as fMRI or PET. Differences in functional imaging data between normal and impaired subject groups can be difficult to interpret because the groups will usually differ in their level of performance; in this case, one cannot tell whether the differences in imaging relate to the underling pathology or the differential performance. Because DTI does not require active participation, group differences are more easily interpreted in terms of underlying pathology. The combination of DTI with functional and structural neuroimaging techniques and postmortem studies should provide novel insights in understanding the neurology of literacy.

EXPERIMENTAL PROCEDURES

Subjects. Subjects in the dyslexic group (5 males and 1 female, age 31.5±5.3 years [mean±SEM]) had a history of developmental dyslexia based on a professional psychological evaluation and reported continued reading difficulties in adulthood. At the time of scanning, 4 subjects exhibited reading scores below, but within 1 SD, of the standardized mean; 2 were more than 1 SD below the mean (Word Identification Subtest)(Woodcock, 1987). Mean reading score on Word ID was 87.3±4.4, and on the Word Attack Subtest (reading of pseudowords) 93.7±5.9. The dyslexic group was significantly impaired on both these tasks compared to the control group (p<0.0003 for word ID and p<0.05 for the Word Attack). The control group included 6 males and 5 females, age 23.1±1.4 years. All subjects were without history of neurological disease. Subjects were right handed, except for one person in the dyslexic group.

MRI acquisition. Scanning was performed with the Signa system (1.5T GE signa Horizon EchoSpeed). Anatomical images were acquired using a T1-weighted, 3D, SPGR volume acquisition, TE/TR=2.0/11.1 ms, field-of-view (FOV) 240×240×186 mm, matrix size=256×256×124 voxels. DTI was performed using a diffusion weighted single shot spin echo, echo planar imaging sequence TE/TR=106 ms/6000 ms, slew rate 120 mT/m/s, delta=32 ms, Δ=34 ms, FOV=360 mm, matrix size 128×128 zerofilled to 256×256. Sixteen axial, 5 mm thick slices (no skip) were imaged. Two b-values were used, b=0 and b=860 s/mm². The high b-value was obtained by applying gradients along two axes simultaneously in a total of six non-collinear directions Eddy current effects in the diffusion weighted images were unwarped using a set of CSF-nulled inversion recovery (TI~2100 ms, b=0 s/mm²) images as a reference. Six apparent diffusion coefficients were calculated, from which the 6 independent elements of the diffusion tensor were determined. From the diffusion tensor, three eigenvectors that define the direction of the diffusion system were determined for each voxel. The eigenvalues $\lambda_1$, $\lambda_2$ and $\lambda_3$, which correspond to the three eigenvectors, represent the magnitude of diffusivity in the three principal directions. Based on these three principal diffusivities and the mean diffusivity ($\lambda$), the fractional anisotropy (FA) was calculated to yield values between 0 and 1:

$$FA = \frac{\sqrt{3}}{\sqrt{2}} \frac{\sqrt{(\lambda_1 - \lambda)^2 + (\lambda_2 - \lambda)^2 + (\lambda_3 - \lambda)^2}}{\sqrt{\lambda_1^2 + \lambda_2^2 + \lambda_3^2}}$$

See P. J. Basser and C. Pierpaoli, "Microstructural and physiological features of tissues elucidated by quantitative-diffusion-tensor MRI," supra. Coherence index for a particular voxel was defined as the mean dot-product of the principal eigenvector, i.e., the vector corresponding to the largest eigenvalue, in that voxel, with the principal eigenvector in its eight neighboring voxels in the same slice. When the eigenvectors are of unity length, the dot product is the cosine of the angle between the pair of vectors.

Data Analysis. Analysis was carried out using Statistical Parametric Mapping software (SPM96, http//:www.fil.ion.ucl.ac.uk/spm). Anisotropy images were spatially coregistered to each individual T1-weighted image, and both anisotropy and T1-weighted (SPGR) images were anatomically normalized to the standard stereotactic space of Talairach and Toumoux using the same parameters. After verifying that there were no group differences in global signal (P>0.40), anisotropy values were scaled to the mean global value. Results were also confirmed using unscaled data. Signal intensity in the T1-images were also normalized. Statistical significance was based on a combination of both Z values in voxels as well as the spatial extent of clusters of voxels having a supra-threshold Z value, providing a significance level of P<0.05, after correction for the large number of comparisons across voxels in the whole brain volume. Two volumes-of-interest (VOIs) were defined as being the clusters of contiguous voxels where there was a significant difference in anisotropy between dyslexic and control subjects. Correlation analysis between reading scores and diffusion anisotropy was also performed with the general linear model implemented in SPM96.

For analysis of direction of axonal orientation, the eigenvector of the diffusion tensor was calculated for each voxel. Sagittal orientation, that is orientation along the anterior-posterior axis, was defined as a voxel having a principal eigenvector with less than 45 degrees deviation from a line passing through the anterior and posterior commissures.

While the invention has been described with reference to specific applications, the description is illustrative of the invention and not limiting the invention. For example, this measure of the structure and organization of the brain can be applied to other disease states and disabilities such as schizophrenia, attention deficit disorders and hyperactivity (ADHD), autism, and other learning disabilities. Thus, various modifications and applications may occur to those skilled in the art without departing from the true spirit and scope of the invention as defined by the appended claims.

What is claimed is:

1. A method of analyzing cerebral white matter in the brain of a living individual for use in evaluating a range of verbal and non-verbal cognitive processing and capacity comprising the steps of:
   a) measuring microstructure of cerebral white matter in the brain using magnetic resonance diffusion tensor imaging (DTI),
   b) determining neuronal fiber integrity in the cerebral white matter from the measured microstructure, and
   c) correlating neuronal fiber integrity to a measure of cognitive processing of the individual to determine the possibility of developing, or the presence of, dyslexia.

2. The method as defined by claim 1 wherein step a) includes determining cerebral white matter diffusion anisotropy.

3. The method as defined by claim 2 wherein the cerebral white matter is confined to the temporo-parietal white matter.

4. The method as defined by claim 1 wherein the cerebral white matter is confined to the temporo-parietal white matter.

5. A method for use in detecting a reading disorder in an individual from cerebral-parietal white matter in the brain of the individual comprising the steps of:
   a) measuring microstructure of the cerebral-parietal white matter using magnetic resonance diffusion tensor imaging (DTI), and
   b) correlating the microstructure to a measure of reading ability of the individual to detect the presence of a reading disorder.

6. The method of claim 5 wherein step a) includes the use of cerebral white matter diffusion anisotropy.

* * * * *